(12) United States Patent
Holman et al.

(10) Patent No.: US 10,016,251 B2
(45) Date of Patent: Jul. 10, 2018

(54) SHIELD FOR PROTECTING A USER FROM RADIATION EMITTED DURING X-RAY IMAGING

(71) Applicant: RADTEC MEDICAL DEVICES, INC., San Carlos, CA (US)

(72) Inventors: Ross Holman, Menlo Park, CA (US); Brian Knott, Palo Alto, CA (US)

(73) Assignee: Radtec Medical Devices, Inc., San Carlos, CA (US)

( * ) Notice: Subject to any disclaimer, the term of this patent is extended or adjusted under 35 U.S.C. 154(b) by 0 days.

(21) Appl. No.: 15/125,578

(22) PCT Filed: Mar. 20, 2015

(86) PCT No.: PCT/US2015/021873
§ 371 (c)(1),
(2) Date: Sep. 12, 2016

(87) PCT Pub. No.: WO2015/148324
PCT Pub. Date: Oct. 1, 2015

(65) Prior Publication Data
US 2017/0004895 A1     Jan. 5, 2017

Related U.S. Application Data

(60) Provisional application No. 61/969,144, filed on Mar. 22, 2014.

(51) Int. Cl.
*G21F 3/02*     (2006.01)
*A42B 3/04*     (2006.01)
(Continued)

(52) U.S. Cl.
CPC .......... *A61B 90/37* (2016.02); *A41D 13/1184* (2013.01); *A42B 3/042* (2013.01);
(Continued)

(58) Field of Classification Search
CPC ..... G21F 1/00; G21F 1/12; G21F 3/02; G21F 3/025
(Continued)

(56) References Cited

U.S. PATENT DOCUMENTS 5,003,300 A    3/1991   Wells
5,038,047 A *   8/1991   Still .................... A61B 6/107
                                                   128/857
(Continued)

OTHER PUBLICATIONS

International Search Report and Written Opinion dated Jun. 29, 2015 for PCT/US15/21873.
(Continued)

*Primary Examiner* — Nicole Ippolito
(74) *Attorney, Agent, or Firm* — Neal Marcus

(57) ABSTRACT

A shield is disclosed for protecting a user from radiation emitted during X-ray imaging. The shield includes a lead layer for absorbing the radiation. The shield comprises first and second opposing flaps configured to position a first portion of the shield around an upper part of the user's head in a deployed configuration, whereby the portion, a component having first and second ends that are attached to the first and second opposing flaps, respectively, wherein the component is adapted to expand to enable the first portion of the shield to adjust to fit around the upper part of the user's head, and third and fourth opposing flaps configured to position a second portion of the shield around a lower part of the user's head.

20 Claims, 7 Drawing Sheets

(51) Int. Cl.
*A61B 90/00* (2016.01)
*A42B 3/30* (2006.01)
*A41D 13/11* (2006.01)
*A42B 3/22* (2006.01)
*A61B 6/10* (2006.01)
*A61F 9/04* (2006.01)
*A62B 17/04* (2006.01)
*G02B 27/01* (2006.01)
*A62B 18/08* (2006.01)
*A61B 90/50* (2016.01)

(52) U.S. Cl.
CPC ............... *A42B 3/225* (2013.01); *A42B 3/30* (2013.01); *A61B 6/107* (2013.01); *A61F 9/04* (2013.01); *A62B 17/04* (2013.01); *G02B 27/0172* (2013.01); *G02B 27/0176* (2013.01); *G21F 3/02* (2013.01); *A61B 2090/372* (2016.02); *A61B 2090/502* (2016.02); *A62B 18/08* (2013.01); *G02B 2027/014* (2013.01)

(58) Field of Classification Search
USPC .......... 250/505.1, 515.1, 516.1, 518.1, 519.1
See application file for complete search history.

(56) References Cited

U.S. PATENT DOCUMENTS

| | | | |
|---|---|---|---|
| 5,875,493 A * | 3/1999 | MacDonald | A01K 55/00 2/10 |
| 6,841,791 B2 | 1/2005 | DeMeo et al. | |
| 7,937,775 B2 | 5/2011 | Manzella, Jr. et al. | |
| 8,621,668 B1 | 1/2014 | Nolz | |
| 2008/0272318 A1 | 11/2008 | Cadwalader et al. | |
| 2011/0272605 A1 | 11/2011 | Cohen | |
| 2013/0300636 A1 | 11/2013 | Cunningham et al. | |

OTHER PUBLICATIONS

International Search Report and Written Opinion dated Jun. 29, 2015 for PCT/US15/21860.

* cited by examiner

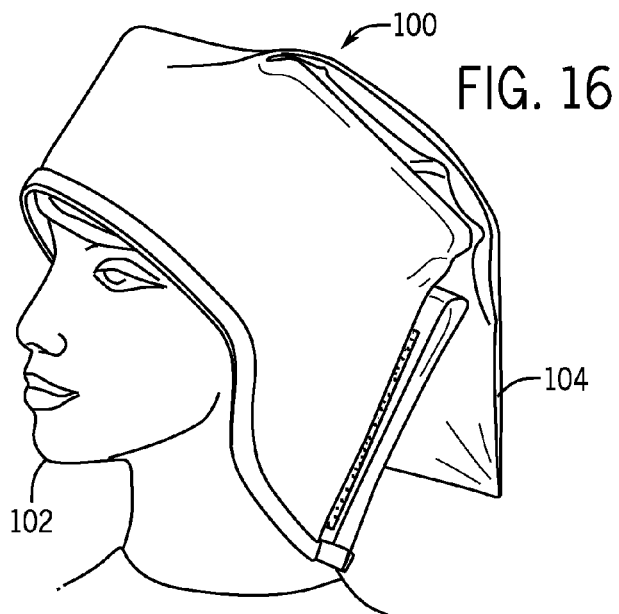
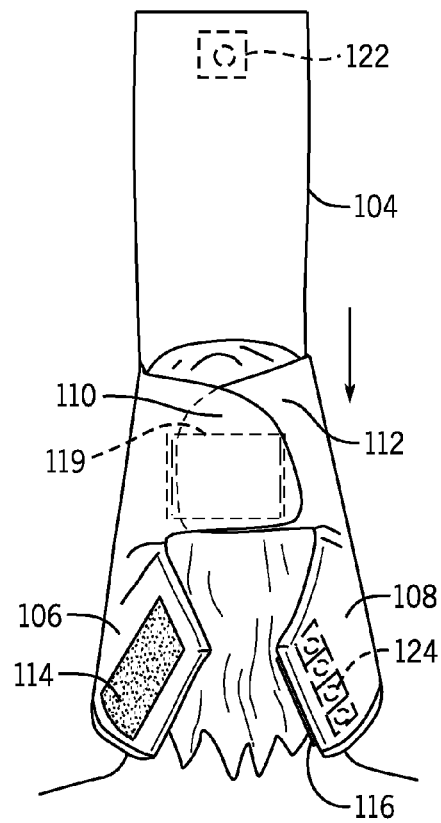
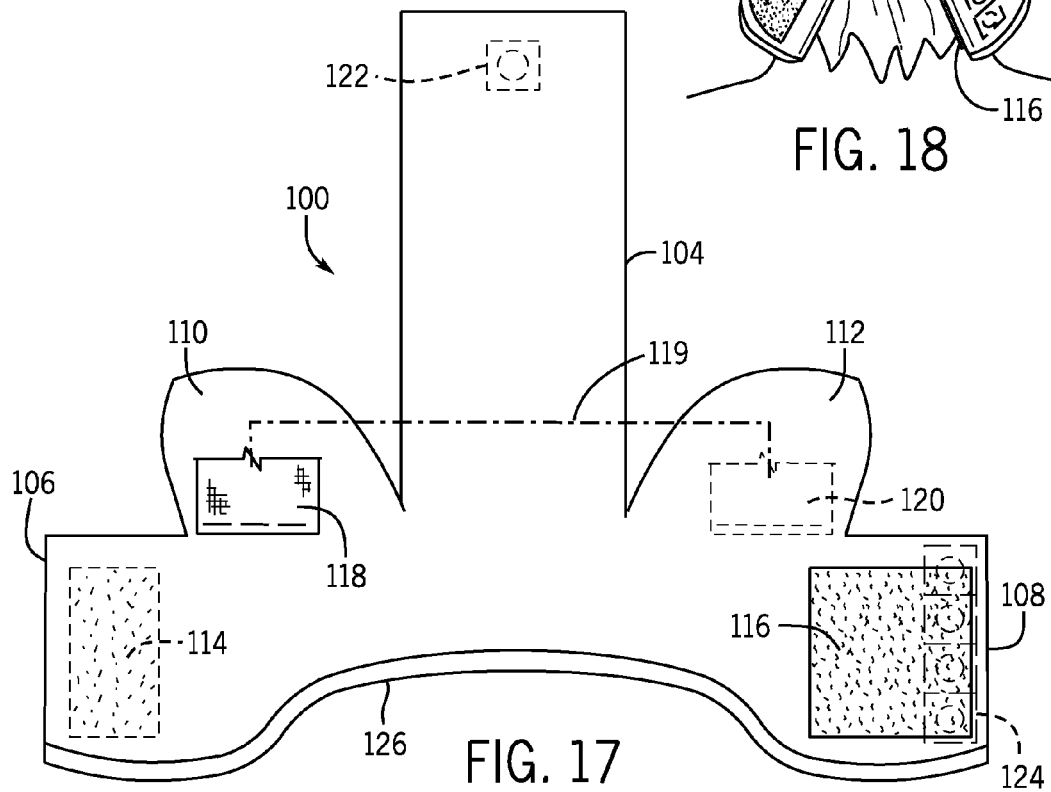

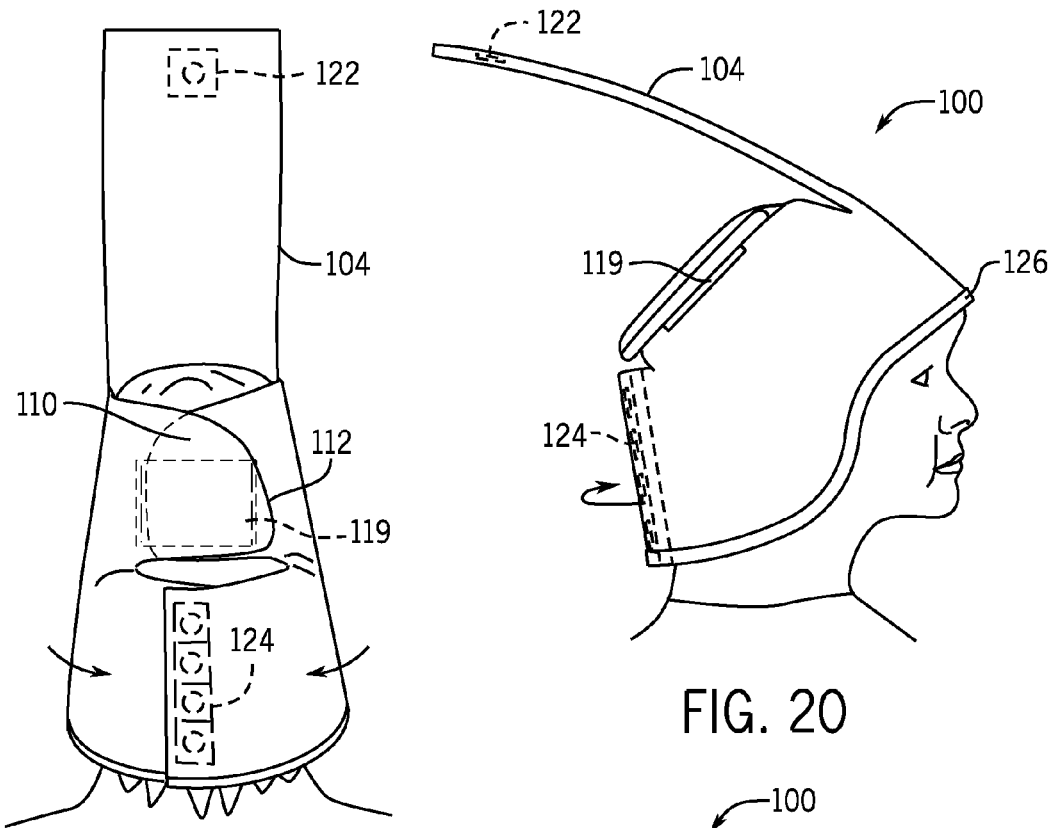
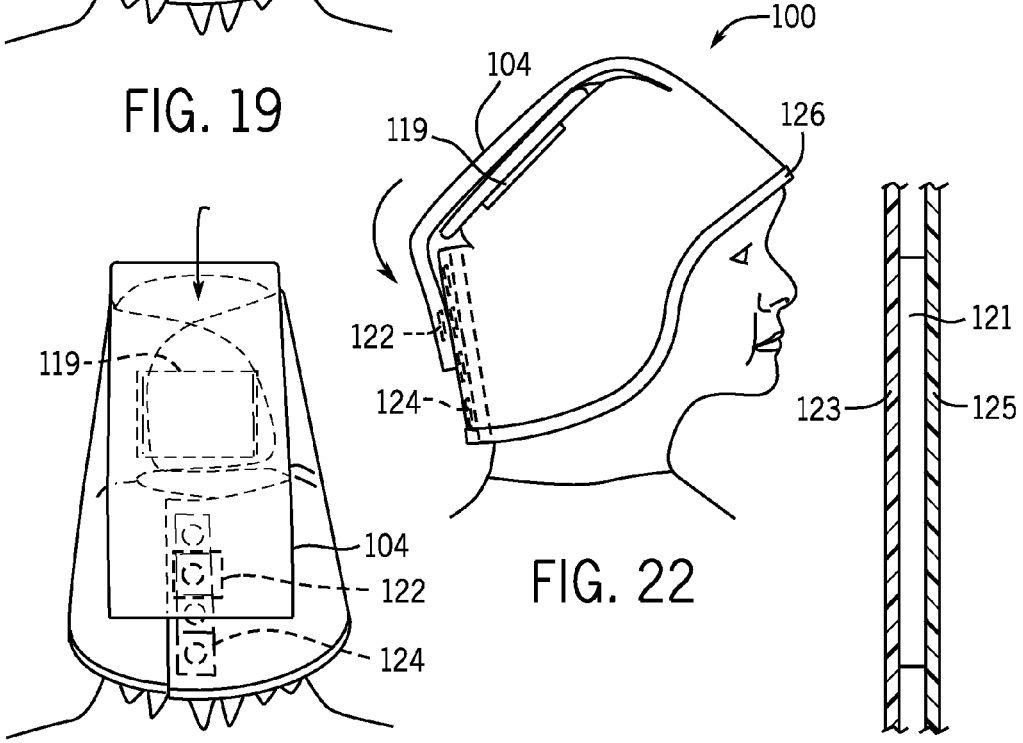
FIG. 19
FIG. 20
FIG. 21
FIG. 22
FIG. 23

SHIELD FOR PROTECTING A USER FROM RADIATION EMITTED DURING X-RAY IMAGING

CROSS-REFERENCE TO RELATED APPLICATIONS

This application claims priority to U.S. provisional application Ser. No. 61/969,144, filed Mar. 22, 2014, entitled "Shield With Display" which is incorporated by reference herein.

FIELD OF THE INVENTION

The present invention relates to a shield for protecting a user from radiation during X-ray imaging.

BACKGROUND OF THE INVENTION

Medical professionals use X-ray (X-radiation or radiography) imaging to assist in the diagnosis of common medical problems. Dental X-rays, for example, are used in the diagnosis of cavities and other common oral problems. While X-ray imaging is helpful in these instances, X-ray imaging unfortunately generates radiation that is absorbed by patients (users) and operators. Long-term radiation exposure has been linked to severe health consequences (e.g., cancer).

It would be thus advantageous to provide a product that would improve upon the disadvantages described above with respect to X-ray imaging.

SUMMARY OF THE INVENTION

Embodiments of a shield for protecting a user from radiation emitted during X-ray imaging are disclosed.

In accordance with another embodiment of this disclosure, a shield is disclosed for protecting a user from radiation emitted during X-ray imaging procedures. The shield includes a layer for reducing the radiation from reaching a head of the user. The shield comprises first and second opposing flaps configured to position a first portion of the shield around an upper part of the user's head in a deployed configuration, and a component having first and second ends that are attached to the first and second opposing flaps, respectively, wherein the component is adapted to expand to enable the first portion of the shield to adjust to fit around the upper part of the user's head.

In accordance with another embodiment of this disclosure, a shield is disclosed for protecting a user from radiation emitted during X-ray imaging. The shield includes a lead layer for absorbing the radiation, the shield comprising first and second opposing flaps configured to position a first portion of the shield around an upper part of the user's head in a deployed configuration, whereby the portion, a component having first and second ends that are attached to the first and second opposing flaps, respectively, wherein the component is adapted to expand to enable the first portion of the shield to adjust to fit around the upper part of the user's head, and third and fourth opposing flaps configured to position a second portion of the shield around a lower part of the user's head.

In accordance with another embodiment of this disclosure, a shield is disclosed for protecting a user from radiation emitted during X-ray imaging. The shield includes a lead layer for absorbing radiation. The shield comprises first and second opposing flaps configured to secure a first portion of the shield around an upper part a head of the user, third and fourth opposing flaps configured to secure a second portion of the shield around a lower part of the head of the user in a substantially circumferential configuration, and a fifth flap to secure the shield around a top of the head of the user.

BRIEF DESCRIPTION OF THE DRAWINGS

FIG. 16 depicts a perspective view of an example shield for protecting a user from radiation emitted during X-ray imaging, the shield shown in an fully deployed configuration on the user's head.

FIG. 17 depicts a top perspective view of the example shield in FIG. 16 wherein the shield is shown in a fully open non-deployed configuration.

FIG. 18-20 depict various stages of deployment of the example shield in FIG. 16.

FIGS. 21 and 22 depict rear and side perspective views of the example shield in FIG. 16 shown in a fully deployed configuration on the user's head.

FIG. 23 depicts a cross-sectional view of the example shield in FIG. 16 wherein the layers are shown.

DETAILED DESCRIPTION OF THE INVENTION

Figure 1:
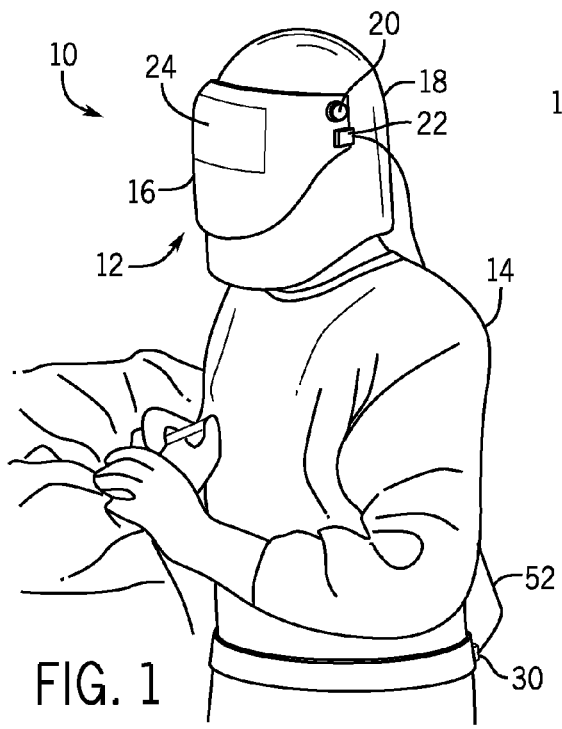
FIG. 1 depicts an example system for receiving, transmitting and displaying data, the system including a device worn by a user.

Embodiments of the present invention are described herein with reference to the drawing figures.

FIG. 1 depicts example system 10 for receiving, transmitting and displaying data. System 10 includes a device 12 that is worn by user 14. Specifically, device 12 is configured to protect user's 14 head and neck (body parts) from debris, radiation and/or other matter during surgery and other medical procedures (e.g., heart surgery, dental procedures, hernia surgery). However, those skilled in the art know that device 12 may also be used to protect a user during non-medical applications. Device 12 includes front shield 16 and rear shield 18. Front shield 16 is configured to protect user's 14 face. Rear shield 18 is configured to protect the remaining part of the user's 14 head (cranium) as well as the user's neck. That is, in this embodiment, rear portion 18 is shaped in the form of a helmet that covers or encloses most of the portions of the neck and head except the user's face (i.e., forehead, left and right lateral sides, hemispherical portion and neck).

Figure 12:
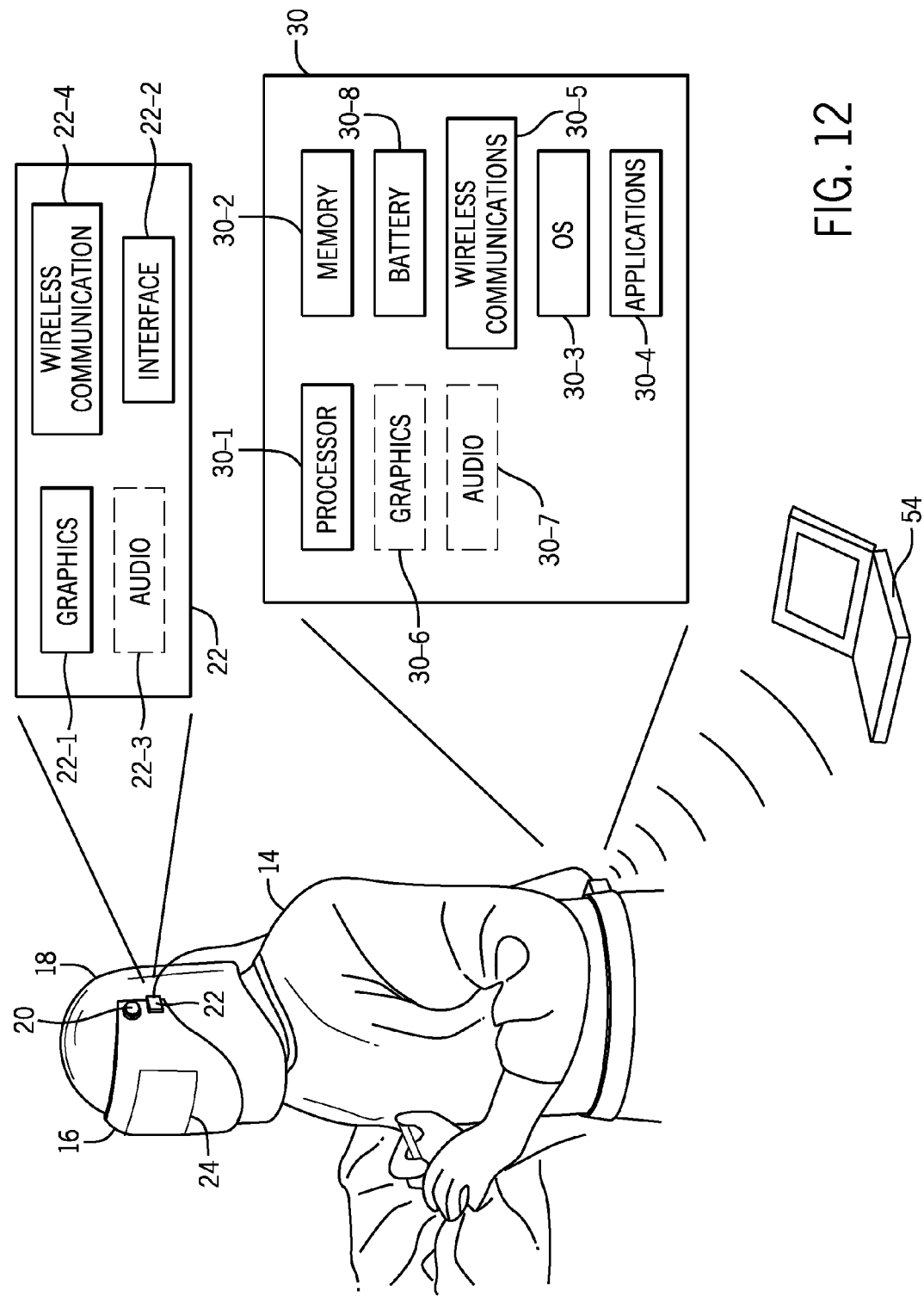
FIG. 12 depicts the system of FIG. 1 wherein the components of graphic and control units are shown.

Device 12 includes pivot joints 20 (pair positioned on opposite sides of front shield 16) that enable front shield 16 to pivot and expose the face of user 14 as needed. Pivot joints 20 may each be a screw/washer/bolt, ball bearing or other assembly that allows front shield 16 to pivot as known to those skilled in the art. In this embodiment, device 12 further includes graphics unit 22 positioned on shield 16 adjacent pivot joint 20, as shown in FIG. 12. Wire 52 couples graphics unit 22 to control unit 30 as described in more detail below.

Figure 2:
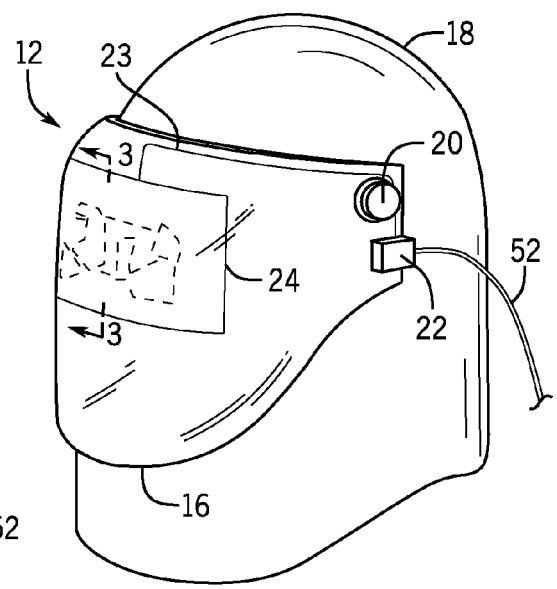
FIG. 2 depicts an enlarged perspective view of the device (only) in FIG. 1.

FIG. 2 depicts an enlarged perspective view device 12 (only) in FIG. 1. Front shield 16 includes several layers, one of which comprises display 24 for displaying content to be viewed by user 14. Graphics unit 22 is coupled to display 24 as described below.

Figure 3:
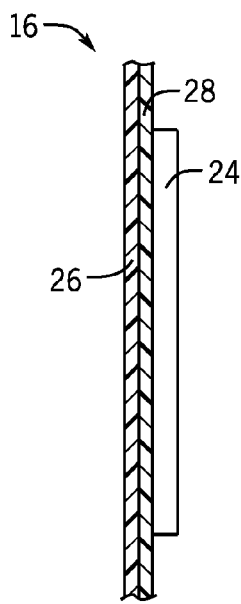
FIG. 3 depicts a cross-sectional view of the device in FIG. 2 along line 3-3.
Figure 4:
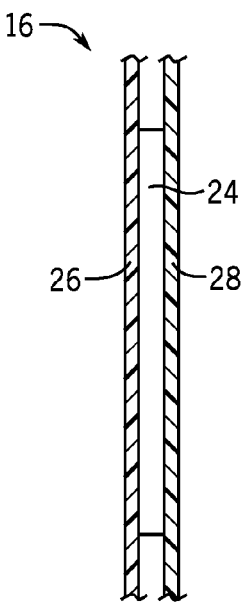
FIG. 4 depicts a cross-sectional view of the device in FIG. 2 along line 3-3 in accordance with another embodiment of the disclosure.
Figure 5:
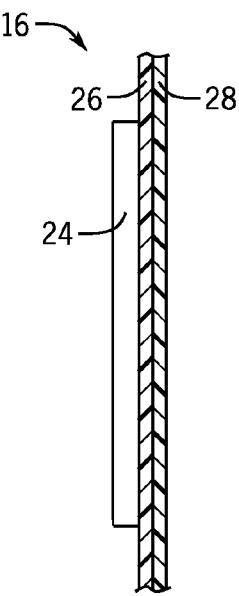
FIG. 5 depicts a cross-sectional view of the device in FIG. 2 along line 3-3 in accordance with yet another embodiment of the disclosure.

FIG. 3 depicts a cross-sectional view of device 12 in FIG. 1 along line 3-3. Display 24 is part of a layer that is actually shown behind layers 26 and 28 (facing user 14). FIG. 4 depicts a cross-sectional view of the device in FIG. 1 along line 3-3 in accordance with another embodiment of the present invention. In FIG. 4, display 24 is shown sandwiched between layers 26 and 28. FIG. 5 depicts a cross-sectional view of the device in FIG. 1 along line 3-3 in accordance with another embodiment of the present invention. In FIG. 5, display 24 is shown in front of layer 26. While display 26 is shown extending (length and width) only a portion of front shield 16, those skilled in the art know that display 24 may be enlarged or reduced in size or positioned to any part of front shield 16. See FIGS. 7 and 9 for example. The layer composition and materials in these embodiments are described in detail below.

As for composition of front shield 16 (in all embodiments of the front shield 16 described in this disclosure), layers 26, 28 are preferably made of acrylic or glass, but those skilled in the art know that other transparent materials and/or compositions may be used to enable a user to view a medical procedure (e.g., surgical or other procedure). If protection is needed from unwanted (direct or scattered) radiation emitted during medical procedures, the acrylic may be leaded acrylic. For example, imaging equipment embedded in a surgical table or robotic arm may emit radiation during a surgical procedure. In this respect, leaded acrylic layer may be any one or more of the layers of front shield 16, but it is preferably a outer layer (i.e., layer 26) and a second layer (e.g., layer 28), if desired. The lead layer is constructed to be at least 0.1 mm in thickness to comply with standards set for radiation protection as known to those skilled in the art. However, those skilled in the art know that the lead layer may be constructed of any thickness as desired. While lead is the preferred material, those skilled in the art know that other materials or compositions may be used to absorb, block, or reduce radiation penetration.

All layers are held together by epoxy/resin (glue) but those skilled in the art know that such layers may be formed in other ways (integrally for example). While front shield 16 is described as multi-layered construction, those skilled in the art know that front shield 16 may be designed with one, two or more layers to achieve desired results.

Display 24 is coupled to graphics unit 22 by way of a set of wires 23 as known to those skilled in the art. Display 24 may be a transparent organic light emitting diode (TOLED) display or any other display having transparent characteristics as known to those skilled in the art. TOLEDs, as known to those skilled in the art, are solid state-semiconductor devices that typically comprise two or more layers (e.g., anode, organic, conducting, emissive, cathode layers). These layers are typically formed as a substrate measuring about 100-500 nanometers thick. TOLED displays are advantageous because they are transparent and are some require limited power consumption. Wire 23 may be copper, fiber optic or other material capable of data transmission as known to those skilled in the art.

Graphics unit 22 is coupled to control unit 30 as shown in FIG. 1. Graphics unit 22 and control unit 30 are described in more detail below with respect to FIG. 12. While TOLED displays are used, those skilled in the art know that display 24 may be constructed of other transparent materials and composition layers. In FIG. 2, display 24 is shown displaying images (data).

Figure 6:
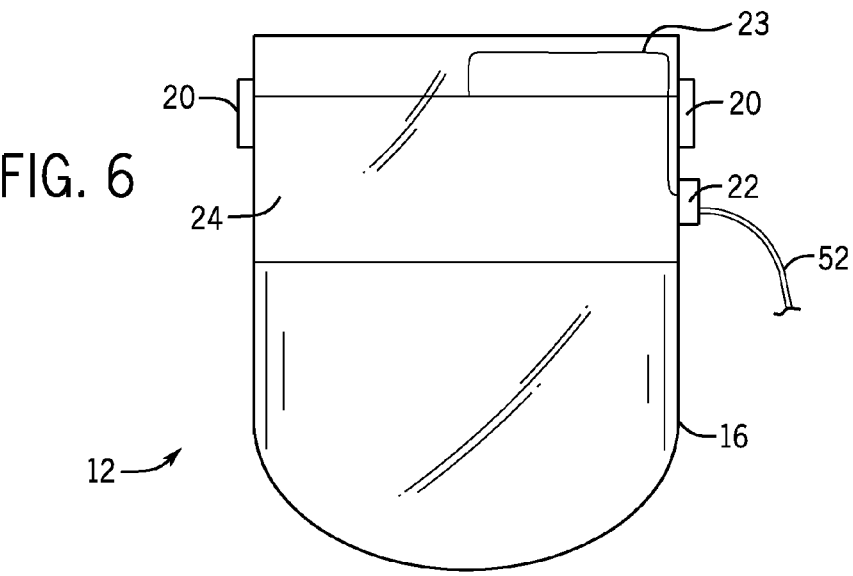
FIG. 6 depicts a front view of the front shield of the device in FIG. 2.

FIG. 6 depicts a front view of device 12 in FIG. 1. As see in FIG. 1, display 24 is positioned within the layer in the upper part of front shield 16. The same reference numerals in FIGS. 1-5 will be also be used in FIGS. 6-15 when possible for consistency and clarity.

Figure 7:
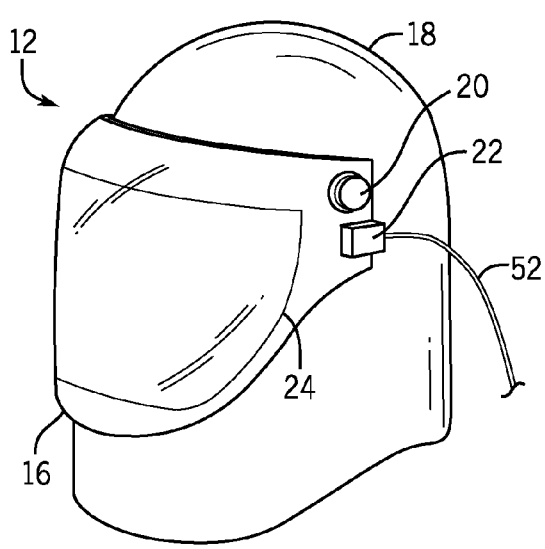
FIG. 7 depicts another example system for receiving, transmitting and displaying data, the system including a device configured to be worn by a user.

FIG. 7 depicts another example system 10 for receiving, transmitting and displaying data, the system including device 12 configured to be worn by a user. In particular, front and rear shields 16 and 18 are similar to those in FIGS. 1 and 2 except display 24 (part of layer) is appropriately sized to extend most of the area of front shield 16. Display 24 is similarly coupled to graphics unit 22 via wires (not shown) as known to those skilled in the art.

Figure 8:
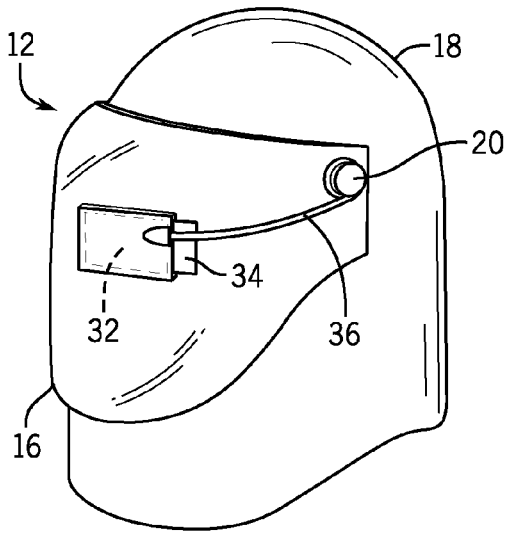
FIG. 8 depicts another example system for receiving, transmitting and displaying data, the system including a device configured to be worn by a user.

FIG. 8 depicts another example system 10 for receiving, transmitting and displaying data, the system including device 12 configured to be worn by a user. In particular, device 12 includes display 32 that extends or disposed in front of front shield 16. Device 12 further includes graphics unit 34 that is shown directly coupled to display 32 itself and pivot arm 36, having a first end mounted to pivot joint 20 and a second end mounted to graphics unit 34 and display 32. Display 32 can either be a TOLED or and LCD or other non-transparent display. Pivot arm 26 is designed to support display 32 in a position to be viewed by a user wearing device 12. Pivot arm 36 is configured to be flexible (adjustable) to enable a user to maneuver (position) display 32 to desired points for proper viewing. A user would merely grasp arm 36 or display 32 and move it to a desired position for viewing (but not interfere with the user's ability to see through front shield 16.) Although graphics unit 34 is attached to or described as part of device 12, graphics unit 34 may be entirely separate from device 12 (but still part of system 10) as known to those skilled in the art.

Arm 36 incorporates or houses the proper wiring to transmit signals and power to and from display 32 as known to those skilled in the art. The wiring exits arm 36 through pivot 20 and extends toward (wiring not shown in FIG. 8) and are coupled to control unit 30 (also not shown in FIG.

8.) Display 32 and graphics unit 34 may be separate components but may also be constructed as a single integral component. Display 34 may be TOLED, LCD or other display as described above. Wire 36 may be copper, fiber optic or other material capable of data transmission as known to those skilled in the art.

Figure 9:
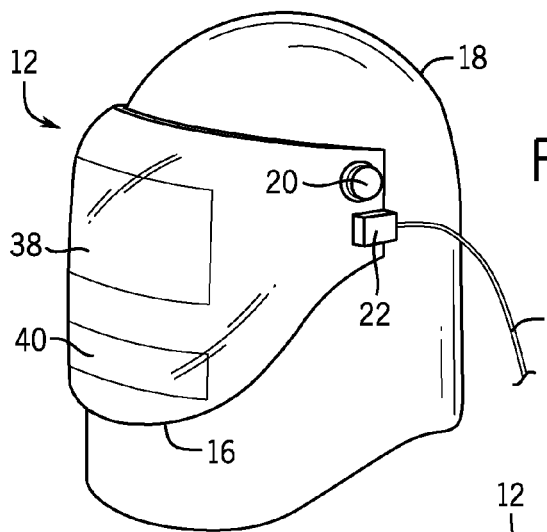
FIG. 9 depicts another example of a system for receiving, transmitting and displaying data, the system including a device configured to be worn by a user.

FIG. 9 depicts another example system 10 for receiving, transmitting and displaying data, the system including device 12 configured to be worn by a user. In particular, device 12 is similar to that shown in FIGS. 1-2 and except one of the layers of front shield 16 includes two displays (or display areas) 38, 40. Otherwise, device 12 functions similarly to device 12 shown in FIGS. 1-2. One or more wires (not shown) couple displays 38, 40 to graphics unit 22 as known to those skilled in the art. In addition, one or more wires similarly couple graphics unit 22 to a control unit located elsewhere as described below.

Figure 10:
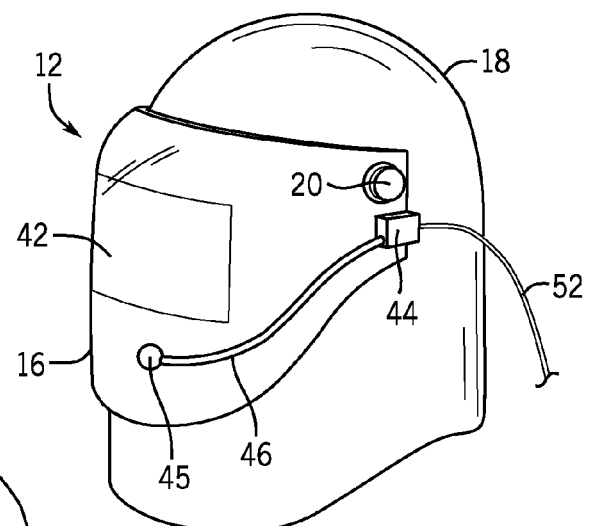
FIG. 10 depicts another example system for receiving, transmitting and displaying data, the system including a device configured to be worn by a user.

FIG. 10 depicts an example of device 12 of system 10 for receiving, transmitting and displaying data, the system including device 12 configured to be worn by a user. In particular, device 12 is similar to that shown in FIGS. 1-2. Front shield 16 has a layer that includes display 42 similar that in shown FIGS. 1-2. Device 12, however, now includes microphone 45 that is coupled to graphics and audio unit 44 by way of adjustable (flexible) arm 46. Adjustable arm 46 houses a wire to enable signal transmission between microphone and graphics and audio unit 44. A wire similarly couples graphics and audio unit 44 to a control unit located elsewhere as described below. In this embodiment, a user may issue commands to generate information, i.e., content (data) for viewing on display 44. While not specifically shown in FIG. 10, shield 16 or rear shield 18 may incorporate a small opening appropriately positioned to enable microphone 45 to receive a user's audio commands. Graphics and audio unit 44 can be also known as a control unit (in addition to control unit 30). The wires disclosed may be copper, fiber optic or other material capable of data transmission as known to those skilled in the art.

In a medical setting such as surgery, examples of basic commands include "show heart rate," "show vitals," "show blood pressure," "show procedure steps," "update status to nurses," (or folders or information, i.e., data), and "show medication list." Other commands include "next screen," "last screen," "enlarge screen," "clear screen," "record," and "stop recording." Those skilled in the art know that many other commands may be used to display desired information or initiate actions to an external computer as discussed below. One or more wires (not shown) couple display 42 to graphics and audio unit 22. In addition, one or more wires similarly couple graphics and audio unit 44 to control unit 30 located elsewhere as described below.

Figure 11:
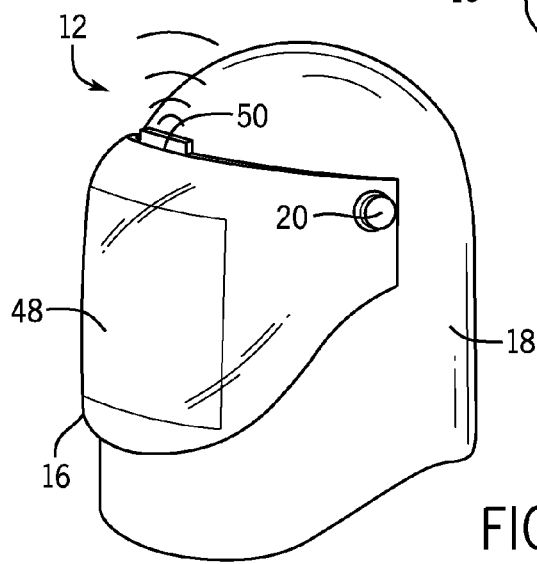
FIG. 11 depicts another example system for receiving, transmitting and displaying data, the system including a device configured to be worn by a user.

FIG. 11 depicts another example of system 10 for receiving, transmitting and displaying data, the system including a device configured to be worn by a user. In particular, device 12 is similar to that shown in FIGS. 1-2. Front shield 16 has a layer that includes display 48 similar to that in FIGS. 1-2. Otherwise, device 12 functions similarly to the device 12 shown in FIGS. 1-2. One or more wires (not shown) similarly couple display 48 to graphics unit 50. However, graphics unit 50 is adapted to communicate wirelessly with control unit 30 located elsewhere (remotely).

As described above with respect to one or more embodiments above, graphics unit 22 is coupled to control unit 30 by wire 52 (also called cable 52). Wire 52 is part of system 10. Graphics unit 22 may alternatively be a graphics and audio unit that also includes audio components and circuitry for the embodiment described herein (FIG. 10). Wire 52 may be copper, fiber optic or other material capable of data transmission as known to those skilled in the art.

FIG. 12 depicts system 10 of FIG. 1 wherein the components of graphics unit 22 and control unit 30 are shown in detail in block diagram format. System 10 includes control unit 30 and wire 52 (as discussed above). Wire 52 is used to couple graphics unit 22 and control unit 30 together. Graphics unit 22 includes a graphics card 22-1. Graphics card 22-1 is used to drive or transmit/interpret data (i.e., information/content) to display 24. Graphics unit 22 may also include one or more interfaces 22-2 for interfacing with circuitry and wires leading to display 24 and control unit 30. As described above, graphics unit 22 may alternatively include audio unit 22-3 (dashed lines) that also incorporates audio components and circuitry (board) to support the embodiment described herein (FIG. 10). Alternatively, the graphics and audio may be combined into one unit. However, these audio components may alternatively be incorporated in control unit 30 as described below. Graphics unit 22 may alternatively include a wireless communication unit 22-4 (dashed lines) to enable graphics unit 22 to communicate with control unit 30 wirelessly.

Control unit 30 includes at least one processor 30-1 and system memory 30-2 (e.g., volatile RAM or non-volatile flash or ROM). Memory 30-2 may include computer readable media that is accessible to the processor 30-1 and may include instructions from processor 30-1, an operating system 30-3 and one or more applications 30-4 to receive and process the data (information/content) for viewing on display 24 or other desired processes such as voice activation and issuing commands as described above. Control unit 20 will also include wireless communication unit 30-5 (circuitry and antenna) to enable control unit 30 to communicate wirelessly to remote computer 54 as known to those skilled in the art. Wireless communication may be achieved using Bluetooth, WIFI or other communication protocols known to those skilled in the art. Control unit 30 may communicate with computer 54 so that a user may request, receive and view content on display 24 as desired. The information (data) may be obtained locally from the computer 54 itself or a server, or via the Internet (with a network of servers) as known to those skilled in the art.

As indicated above, graphics circuitry is incorporated in graphics unit 22. However, those skilled in the art know some or all graphics circuitry in unit 30-6 (dashed lines) may be incorporated within control unit 30. The same holds true for audio unit 30-7 (dashed lines). Control unit 30 also includes battery 30-8 to power control unit 30, graphics unit 22 and ultimately display 24. Battery 30-8 may be lithium or other suitable power mechanism. Alternatively, control unit 30 may be powered by a remote power source (battery or wall socket) coupled by wire as known to those skilled in the art.

Computer 54 is a general-purpose computer to support the embodiments of the systems and methods disclosed in this application. In a particular configuration, the general purpose computer is shown as a laptop but it may be a desktop or server configured to enable part or all of the execution of the software stored in such computer. Computer 54 typically includes at least one processor and memory (e.g., volatile RAM or non-volatile flash or ROM). The memory may include computer readable media that is accessible to the processor and may include instructions for the processor, an operating system and one or more applications such as Java and any part of an application software. Computer 54 will include (1) one or more communication connections such as network interfaces to enable the computer to communicate with control unit 30 and/or other computers over a network, (2) storage such as a hard drive or solid state drives (SSD), (3) video cards and (4) other conventional components known to those skilled in the art. Computer server typically runs Unix or Microsoft as the operating system and include TCP/IP protocol stack (to communicate) for communication over the Internet as known to those skilled in the art. Computer program data is also stored within computer 54. The components of computer 54 are now shown.

As described above, FIGS. 1-12 depict device 12 in which rear shield 18 is shown. Like front shield, rear shield 18 may be designed to protect a user's head from human and other debris during surgery. However, shield 18 may be constructed of many different materials depending upon its application. For surgical use, shield 18 may be constructed of several layers (of possibly many composite materials) including lead to protect a user from unwanted (direct or scattered) radiation that is typically emitted by X-ray imaging and other imaging and monitoring equipment. Such equipment may be embedded in an operating table itself or part of a free standing or mountable robotic armatures. Lead layer is approximately 0.5 mm thick to protect against unwanted (direct or scattered) radiation. However, those skilled in the art know that other thicknesses and materials other than lead may be used to achieve desired results and standards.

Figure 13:
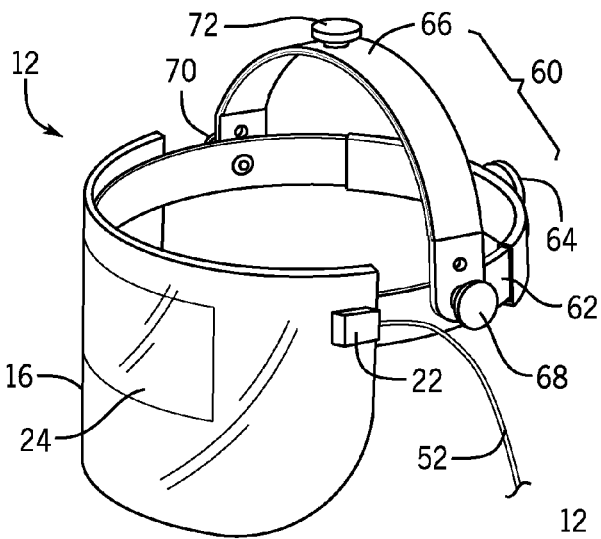
FIG. 13 depicts another example system for receiving, transmitting and displaying data, the system including a device configured to be worn by a user.

FIG. 13 depicts another example system 10 for receiving, transmitting and displaying data, the system including device 12 configured to be worn by a user. In particular, device 12 includes front shield 16 that is constructed similar to front shield 16 in FIGS. 1-2. While it is shaped differently, front shield 16 has a multi-layered construction, at least one of which includes display 24 for displaying information/content (data) to a user. Details of the composition of display 24 is discussed above. Therefore, it will not be discussed here. Graphics unit 22 and wire 52 are similarly positioned and configured as described above.

Device 12 further includes head mount 60 (apparatus) that enables a user to mount (i.e., wear) device 12 to the user's head. Head mount 60 comprises circumferential band 62 that fits around the (horizontal) circumference of a user's head and adjustable knob 64 to enable a user to (expand or retract) increase or decrease the circumference of band 62 to fit variable head circumferences as known to those skilled in the art. Head mount 60 further comprises vertical lateral band 66, adjustable knobs 68, 70 and adjustable band 72. Lateral (vertical) band 66 is configured to be semi-circular in size to fit around the top of a user's head from ear to ear. Adjustable knobs 68, 70 are constructed to enable lateral band 66 to pivot (rotate) along an arc or circumference of the top of a user's head. Adjustable knob 72 may be rotated to enable band 66 to (expand or retract) increase or decrease the circumference of band 66 as known to those skilled in the art. In use, a user may adjust adjustable knobs 68, 70 to enable the user to maneuver band 66 to rest on a particular location on the top of a user's head and adjust knob 72 to increase or decrease band 66 circumference to fit the top circumference of the user's head from ear to ear. A user may adjust adjustable knob 64 to enable a user to increase or decrease band 62 to fit the horizontal circumference of a user's head. While head mount 60 is described as having two bands for proper fitting, those skilled in the art know that one band or multiple bands (3 or more) may be used to achieve desired results.

Figure 14:
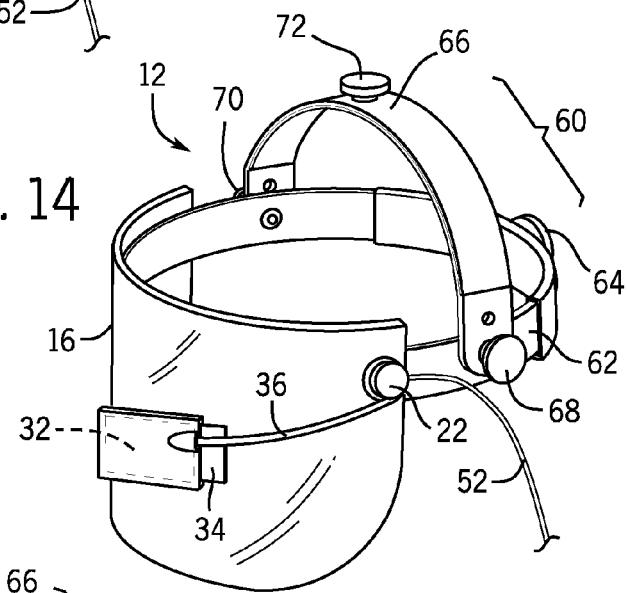
FIG. 14 depicts another example system for receiving, transmitting and displaying data, the system including a device configured to be worn by a user.

FIG. 14 depicts another example system 10 for receiving, transmitting and displaying data, the system including device 12 configured to be worn by a user. In particular, device 12 is similar the device shown in FIG. 13, but front shield 16 does not incorporate a display within a layer of shield 16. Device 12 includes display 32, graphics unit 34 and arm 36 as shown in FIG. 8 and described above. These components function similarly so they won't be described here.

Figure 15:
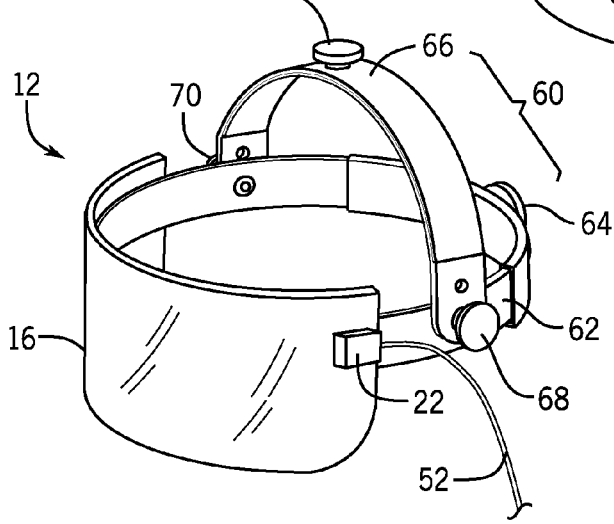
FIG. 15 depicts another example system for receiving, transmitting and displaying data, the system including a device configured to be worn by a user.

FIG. 15 depicts another example system 10 for receiving, transmitting and displaying data, the system including device 12 configured to be worn by a user. In particular, device 12 is similar the device shown in FIG. 13, except that the shield 16 is smaller in scale to nursing or other applications that require lighter weight with less protection. The display encompasses the majority of the surface area of shield 16.

As described above, the displays in the embodiments in FIGS. 1-7, 10-13, and 15 have transparent characteristics (properties). The displays in the embodiments in FIGS. 8 and 14 may have transparent or non-transparent characteristics. Display 38 in the embodiment in FIG. 9 will have transparent characteristics while display 40 may or may not have transparent characteristics.

FIGS. 16-23 depict various views of shield 100 in accordance with another embodiment of this disclosure. Shield 100 is configured to protect a user's (patient's) head (e.g., forehead, right and left lateral sections) and neck from unwanted (direct or scattered) radiation during X-ray imaging (such dental X-ray imaging, computerized tomography (CAT SCAN), mammograms and other medical procedures). Shield 100 is a single fully adjustable construction that fits upon a user's head as described below.

FIG. 16 depicts a side perspective view of an example shield 100 for protecting a user from radiation emitted during X-ray imaging. That is, FIG. 16 depicts shield 100 deployed in a usable configuration on user 102. Shield 100 as shown exposes user's 102 face to enable a dentist, his or her assistant, nurse or other medical professional to take X-rays of user's mouth, while covering and protecting the remaining portion of user's head (patient). Shield 100 extends essentially from a user's forehead and covers much of a user's head and neck.

FIG. 17 depicts a top perspective view of the example shield in FIG. 16 wherein shield 100 is shown in its fully unexpanded configuration, resting flat against a surface. Shield 100 includes a plurality of flaps for proper deployment. The plurality of flaps include long flap 104, distal opposing flaps 106, 108 (lower flaps), and opposing clover shaped flaps 110, 112 (upper flaps). Long flap 104 is used to wrap and cover the top, hemispherical portion of user's 102 head (including crown). Long flap 104 extends generally perpendicular to the part of shield 100 between distal opposing flaps 106, 108. Flap 104 is shown in a generally rectangular shape. However, those skilled in the art know that flap 104 may have any shape to achieve desired results. For example, flap 104 may have with inward tapered side edges or outward tapered side edges (toward the top edge).

In brief, distal opposing flaps 106, 108 are used to cover part of the neck. In addition, flaps 106, 108 cause a portion of shield 100 to cover lower right and left lateral sides of the user's head including the user's ears. Clover shaped flaps 110, 112 are used to cause a portion of shield 100 to cover forehead and the upper right and left lateral sides of the head (including the temporal region). In FIG. 17, distal opposing flaps 106,108 are generally linear with respect to each other in an open un-deployed configuration (although not shown, the band is depicted as a dashed line) and are essentially perpendicular with respect to flap 104 as best shown in FIG. 17. This is described in more detail below.

Distal opposing flaps 106, 108 incorporate opposing mating (attaching) elements 114, 116 that appear on opposite sides of shield 100. Elements 114, 116 function to secure flap 106 to flap 108. Clover shaped flaps 110, 112 include opposing (attaching) elements 118, 120 that are secured to opposing surfaces of shield 100. Shield 100 includes elastic band 119 (depicted in dashed lines in FIGS. 17-22) that has distal ends that are fastened to elements 118, 120, respectively. Elements 118, 120 are separate pieces directly attached to clover shaped flaps 110, 112 (e.g., stitched or bonded) as shown. Alternatively, elastic band 119 may be directly attached to the surface or one or more layers of shield 100 as known to those skilled in the art (e.g., stitched or bonded). Band 119 is configured to expand and subsequently contract to its original state as known to those skilled in the art. Flaps 110, 112 are configured, i.e., arranged in an overlapping configuration, and when shield 100 is advanced over a user's head, band 119 expands and shield 100 enlarges to receive the user's head. In this embodiment, elastic band 119 is intended to maintain tension between flap 110 and flap 112 (i.e., pull these flaps together around the head).

The distal ends of elastic band 119 are designed to be permanently fixed to shield 100 at elements 118, 120, but those skilled in the art know that band 119 may be configured to be removable and/or adjustable to achieve desired results. As discussed above, elastic band 119 is used in this embodiment maintain tension, but those skilled in the art know that any other part, element, component or piece may be used that is adapted to stretch or expand to enable the upper part of shield to expand to accommodate various head size circumferences and contract when not in use). The size of the band is designed to ensure that the circumference of shield 100 is typically smaller than the average adult or child size so that shield 100 will snuggly fit the head of most users.

Alternatively, elements 118, 120 may be fastened together directly (self mating) as known to those skilled in the art. In this respect, shield may be designed for specified head sizes. As indicated, flaps 110, 112 are clover shaped, but those skilled in the art know that these flaps may be circular, square or other shapes to achieved desired results.

Flap 104 includes element 122 which is adapted to attach to mating (attaching) element 124 that appears on the opposite surface of flap 108 (opposite side of shield 100). Element 124 is shown in FIG. 22 in dashed lines. Edge 126 is designed to track across the edge of a user's forehead above a user's supraorbital foramen bone. Mating element 122 is a single magnet element while element 124 is a linear strip of magnet elements embedded within the material of flap 108 using techniques known to those skilled in the art.

Self mating (attaching) elements 114,116 are typically Velcro mating pieces as known, but these elements may be any suitable material that enables the opposing flaps to mate and secure to each other as known to those skilled in the art. While opposing magnets are used as mating elements 122, 124, those skilled in the art know that these elements may be mating Velcro pieces, snap pieces or any other material suitable to secure to one another.

In application, user 102 will position or align edge 126 of shield 100 along his/her forehead while fitting the upper section around the user's head. Specifically, the user will then slide and advance shield 100 portion between opposing clover shaped flaps 110, 112 onto a user's head, thereby expanding band 119. In this position, a portion of shield 100 is positioned around the upper part of the user's head when the user's head is in an upright position, as shown in FIG. 18. In this embodiment, flaps 110, 112 are in an overlapping configuration upon the crown of the user's head. (In alternative embodiments, flaps 110, 112 may be configured to lie directly on top of the user's head in a deployed configuration while flaps 106, 108 will function as described herein.) Elastic band 119 maintains tension between flaps 110, 112 to enable the shield 100 to adjust to fit snuggly and properly around variable head sizes. Then, user 102 pulls flaps 106, 108 together in the rear of the user's head (FIG. 18), to thereby cause a portion of shield 100 to wrap around the lower part of the user's head and neck. In this respect, this portion of shield 100 is in a circumferential configuration. That is, shield 100 is positioned to cover the right and left lateral sides of user's 102 head (i.e., covering a forehead, temporal region, ears and rear region of user's 102 head). Elastic band 119 maintains tension across user's 102 head. User 102 will then secure element 114 to element 116, whereby shield 100 now fits snuggly around the user's head. This is best shown in FIG. 19.

As indicated above, flaps 110, 112 are held together using elastic band 119 or another method of tacking or fastening, as known to those skilled in the arts. Flaps 106, 108 are held together in the rear of the head of user 102 using mating elements 114, 116. These elements are shown best in FIGS. 16-20. User 102 will then grasp flap 104, pull it over the hemispherical portion of the head (over the crown) and toward the rear of the head and down over secured flaps 106,108. Mating elements 114 and 116 are used to secure flap 106 to flap 108, thereby ensuring that flap 104 fully covers any exposed areas on the top of user's 102 head. This is shown in FIGS. 20-21. The final deployed shield 100 on user 102 is shown in an essentially frustum configuration (except that that base and top are not quite parallel planes).

Shield 100 has a multiple layer construction. In one embodiment, one layer comprises a lead or lead alternative layer, sealed between two rubber layers. In this embodiment, the rubber and lead layers are free floating between two outer layers. Alternatively, rubber coated lead or vinyl coated lead layers may between the outer layers. The outer layers may be made of ballistic nylon, vinyl or other durable material known to those skilled in the art. The outer layers are stitched, molded or attached together along the edges thereof. FIG. 23 depicts a cross-sectional view of the example shield in FIG. 16 wherein the layers are shown. In this embodiment, lead layer 121 is rubber coated lead sandwiched between two vinyl outer layers 123, 125 stitched along the edges thereof.

In the embodiments of shield 100, lead layer is at least 0.25 millimeter (mm) thick as required to satisfy the certain standards for protecting users from radiation. Lead layer thickness is typically 0.3-0.5 mm for adults and 0.5-1 mm for children. With these thickness ranges, 95-98% of the direct and scattered radiation is absorbed by the lead layer, thereby blocking or reducing the quantity of radiation from reaching the user's covered body areas. However, those skilled in the art know that the lead may be any thickness as desired. The number of layers may vary depending on use and manufacture as known to those skilled in the art. The assembly of layers creates a composite configuration, i.e., a single one-piece construction of shield 100. Alternatively, those skilled in the art know that the layers of shield 100 may be constructed as a one integral piece or several integral pieces connected together. Shield 100 may be manufactured in two sizes, one to fit an adult and the other to fit a child. However, those skilled in the art know that shield 100 may be manufactured in multiple sizes and thicknesses.

As described above, shield 100 is designed to protect a user from radiation during X-ray imaging (such dental X-rays, computerized tomography (CAT SCAN, mammograms and other medical procedures known to those skilled in the art). Thus far, shield 100 is described and shown exposing a user's face (below his/her forehead) in fully deployed configuration. This will enable a dentist or other professional to take X-rays of the areas surrounding the cheek and jaw to view a user's teeth and other body parts. In other embodiments, however, shield 100 may be designed to cover a user's eyes, nose and/or other areas on the face that are not intended for X-ray imaging.

It is to be understood that the disclosure teaches examples of the illustrative embodiments and that many variations of the invention can easily be devised by those skilled in the art after reading this disclosure and that the scope of the present invention is to be determined by the claims below.

What is claimed is:

1. A shield for protecting a user from radiation emitted during X-ray imaging, the shield including a layer for reducing the radiation from reaching a head of the user, the shield having an edge with a portion thereof that is configured to extend across a forehead above eyes of the user when the shield is in a deployed configuration on the user's head, thereby exposing a user's face to enable X-ray images to be taken of the user's face including a mouth and/or jaw of the user, the shield comprising:
    first and second opposing flaps configured to position a first portion of the shield around an upper part of the user's head in the deployed configuration; and
    a component having first and second ends that are attached to the first and second opposing flaps, respectively, wherein the component is adapted to expand, in the rear of the user's head as the shield is advanced on the user's head to enable the first portion of the shield to adjust to fit around the upper part of the user's head.

2. The shield of claim 1 wherein the first and second opposing flaps are arranged in an overlapping configuration.

3. The shield of claim 1 further comprising:
    third and fourth opposing flaps configured to position a second portion of the shield around a lower part of the user's head.

4. The shield of claim 3 wherein the third and fourth opposing flaps are arranged in an overlapping configuration in a deployed configuration on the user's head.

5. The shield of claim 3 further comprising:
    a fifth flap configured to wrap around a top part of the head of the user, over the first and second opposing flaps in the deployed configuration.

6. The shield of claim 1 wherein the component is an elastic band that is adapted to stretch to enable the portion of the shield to snuggly fit around the upper part of the user's head.

7. The shield of claim 1 wherein the layer is a lead layer for absorbing radiation.

8. The shield of claim 1 wherein the first portion of the shield around the upper part of the user's head comprises a portion of the layer for reducing the radiation.

9. The shield of claim 3 wherein the second portion of the shield around the lower part of the user's head comprises a portion of the layer for reducing the radiation.

10. The shield of claim 5 wherein the fifth flap around the top part of the user's head comprises a portion of the layer for reducing the radiation.

11. The shield of claim 3 wherein the third and fourth opposing flaps are further configured to position a fourth portion of the shield around a part of the user's neck.

12. The shield of claim 3 wherein the third and fourth opposing flaps includes first and second mating elements on opposite sides thereof respectively, whereby the first and second elements are adapted to mate with each other to secure the portion of the shield around the lower part of the user's head.

13. The shield of claim 5 wherein the fifth flap has an end that is adapted to attach to one of the third and fourth opposing flaps in the deployed configuration on the user's head.

14. A shield for protecting a user from radiation emitted during X-ray imaging, the shield including a lead layer for absorbing the radiation, the shield having an edge with a portion thereof that is configured to extend across a forehead above eyes of the user when the shield is in a deployed configuration on the user's head, thereby exposing a user's face to enable X-rays to be taken of the user's face including a mouth and/or jaw of the user, the shield comprising:
    first and second opposing flaps configured to position a first portion of the shield around an upper part of the user's head in the deployed configuration;
    a component having first and second ends that are attached to the first and second opposing flaps, respectively, wherein the component is adapted to expand in the rear of the user's head as the shield is advanced on the user's head to enable the first portion of the shield to adjust to fit around the upper part of the user's head; and
    third and fourth opposing flaps configured to position a second portion of the shield around a lower part of the user's head.

15. The shield of claim 14 further comprising:
    a fifth flap configured to wrap the shield around a top part of the head.

16. The shield of claim 15 further comprising:
    a fifth flap configured to wrap around a top part of the head of the user, over the first and second opposing flaps in the deployed configuration.

17. The shield of claim 16 where the component is an elastic band that is adapted to stretch to enable the first portion of the shield to snuggly fit around the upper part of the user's head.

18. A shield for protecting a user from radiation emitted during X-ray imaging, the shield including a lead layer for absorbing radiation, the shield having an edge with a portion thereof that is configured to extend across a forehead above eyes of the user when the shield is in a deployed configuration on the user's head, thereby exposing a user's face to enable X-ray imaging to be taken of the user's face including a mouth and/or jaw of the user, the shield comprising:
    first and second opposing flaps configured to secure a first portion of the shield around an upper part a head of the user;
    a component engaging the first and second flaps so as to enable the first portion of the shield to adjust to fit around the upper part of the user's head as the shield is advanced to the deployed configuration;
    third and fourth opposing flaps configured to secure a second portion of the shield around a lower part of the head of the user in a circumferential configuration; and
    a fifth flap to secure the shield around a top of the head of the user.

19. The shield of claim 18 wherein the component comprises first and second mating elements attached to the first and second flaps.

20. The shield of claim 19 wherein the component comprises an elastic band adapted to expand to fit around the user's head.

* * * * *